(12) United States Patent
Salonen (10) Patent No.: US 6,242,186 B1
(45) Date of Patent: Jun. 5, 2001

(54) METHOD FOR DETECTING A RISK OF CANCER AND CORONARY HEART DISEASE AND KIT THEREFOR

(75) Inventor: Jukka Salonen, Jännevirta (FI)

(73) Assignee: Oy Jurilab Ltd., Jannevirta (FI)

( * ) Notice: Subject to any disclaimer, the term of this patent is extended or adjusted under 35 U.S.C. 154(b) by 0 days.

(21) Appl. No.: 09/323,482

(22) Filed: Jun. 1, 1999

(51) Int. Cl.$^7$ ............... C12Q 1/68; C12P 19/34; C07H 21/04
(52) U.S. Cl. ............ 435/6; 435/91.1; 435/91.2; 536/22.1; 536/24.3
(58) Field of Search ............. 435/6, 91.2, 91.1; 536/22.1, 24.3

(56) References Cited

U.S. PATENT DOCUMENTS 5,652,106 * 7/1997 Plikaytis et al. ............ 435/6

OTHER PUBLICATIONS

Schmidt et al. Paraoxonase PON1 polymorphism Leu–Met54 is associated with carotid atherosclerosis results of the austrian stroke prevention study, Stroke, vol. 29 (10), p. 2043–2048, 1998.*

M. Navab et al., Arterioscler Thromb Vasc Biol, 16:831–42 (1996).
M.I. Mackness et al., Atherosclerosis, 104:129–135 (1993).
A.D. Watson et al., J. Clin Invest, 96:2882–91 (1995).
B.N. La Du et al., Chem Biol Interact, 87(1–3):25–34 (Jun. 1993).
R. Humbert et al., Nature Genet, 3:73–6 (1993).
M.I. Mackness et al., Curr Opin Lipidol, 7:69–76 (1996).
M.I. Mackness et al., Lancet, 349:851–2 (1997).
B. Mackness et al., Lancet, 353:468–9 (1999).
M.C. Garin et al., J. Clin Invest, 99:62–6 (1997).
B. Mackness et al., Br J Pharmacol, 122:265–8 (1997).
T. Zama et al., Arterioscler Thromb Vasc Biol, 17:3565–9 (1997).

* cited by examiner

Primary Examiner—W. Gary Jones
Assistant Examiner—Joyce Tung
(74) Attorney, Agent, or Firm—Birch, Stewart, Kolasch & Birch, LLP (57) ABSTRACT

The present invention is directed to a method and a kit for detecting a risk of cancer and coronary heart disease in a subject, comprising isolating genomic DNA from said subject, determining the allelic pattern for the codon 54 of the paraoxonase encoding PON1 gene in the genomic DNA, identification of M54L mutation indicating said risk being reduced.

6 Claims, 2 Drawing Sheets

Days from baseline to first acute coronary event

FIG.4

Days from baseline to first acute coronary event

METHOD FOR DETECTING A RISK OF CANCER AND CORONARY HEART DISEASE AND KIT THEREFOR

FIELD OF THE INVENTION

The present invention relates to a method for detecting or predicting the risk of, or predisposition to, cancer and coronary heart disease in a subject. The present invention also relates to a kit for carrying out the said method.

BACKGROUND OF THE INVENTION

Oxidative stress and free radicals have been implicated in the etiology of a number of diseases, including cancers, coronary heart diseases and type II diabetes. The human body has a number of endogenous free radicals scavenging systems which have genetic variability. The serum paraoxonase (PON) is an enzyme carried in the HDL that contributes to the detoxification of organophosphorus compounds but also of carcinogenic products of lipid peroxidation. Paraoxonase has been suggested to account for an important part of the antioxidative properties of HDL[1-3]. PON1 is polymorphic in human populations and different individuals also express widely different levels of this enzyme.[4-7]

Two polymorphisms are currently known in human PON1. The Q191R polymorphism was the first mutation of PONI reported.[4,6] The second one is the missense mutation of A to T in codon 54, producing a substitution of methionine (M) to leucine (L) (Met45Leu[4a]; known also as Met55Leu[4]). Both these polymorphisms have been shown to affect serum PON activity,[6,8,9] and in particular, the L54 allele has been associated with an increased PON activity. There are a few previous studies concerned with the association of Met54Leu polymorphism and coronary heart disease (CHD), the findings are, however, inconclusive[8]. To our knowledge, only two studies concerning the association of the Met54Leu polymorphism with CHD have been published.[8,10] In a cross-sectional study, the prevalence of LL homozygosity was twofold among diabetics who already had clinical CHD compared with diabetics who had no clinical CHD, even though LL homozygotes had 1.7-fold PON activity, compared with MM homozygotes.[8] In a Japanese retrospective case-control study, Met54Leu PON polymorphism had no association with CHD.[10]

SUMMARY OF THE INVENTION

The present invention was based on the hypothesis that homozygosity of the L54 allele in the PON1 gene might protect against certain diseases associated with oxidative stress, in particular cancer and coronary heart disease. For this purpose, the said hypothesis was tested in a prospective population-based cohort study. The results of this study show that our hypothesis is true and that there is a clear association between homozygosity of the L54 allele, and a reduced risk for cancer and coronary heart disease.

The present invention is thus directed to a method for detecting a risk of cancer and coronary heart disease, in a subject, comprising isolating genomic DNA from said subject, determining the allelic pattern for the codon 54 of the paraoxonase encoding PON1 gene in the genomic DNA, and identification of M54L mutation indicating said risk being reduced.

The present invention is also directed to a kit for detecting a risk of cancer and coronary heart disease in a subject, comprising means for determining the allelic pattern for the codon 54 of the paraoxonase encoding PON1 gene in a genomic DNA sample, and means for carrying out a comparison of the allelic pattern so determined to a control sample.

DETAILED DESCRIPTION OF THE DRAWING

In the drawing.

DETAILED DESCRIPTION OF THE INVENTION

Determination of the Allelic Pattern

The method according to the invention for determining the allelic pattern of the codon in question, is preferably carried out as a polymerase chain reaction, in accordance with known techniques.[4]

Specifically, genotyping was done by extracting DNA from EDTA blood with a salting-out method after lysing red cells with 10 mM NaCl/10 mM EDTA. A 170-bp DNA-fragment of PON1 gene was amplified with PTC-100 thermal cycler (MJ Research Inc., Massachusetts, USA) using the oligonucleotide primers as described by Humbert et al.[4] namely 5'GAAGAGTGATGTATAGCCCCAG3'(SEQ ID No: 1) and 5'TTTAATCCAGAGCTAATGAAAGCC3'(SEQ ID No: 2). The PCR mixture contained 10 mM Tris-HCl (pH 8.8), 50 mM KCl, 1.5 mM $MgCl_2$, 0.1% Triton X-100, 200 $\mu$M each of the four deoxynucleotides, 0.5 $\mu$M each of the primers, 1 U Dynazyme (Finnzymes, Inc., Finland) in a final volume of 50 $\mu$l. After initial denaturation at 96° C. for 2.5 min, DNA was amplified by 39 cycles: denaturation at 96° C. for 30 s, annealing at 61° C. for 1 min and extension at 72° C. for 1 min, followed by a 6 min final extension. The Hsp92II enzyme digestion was done as recommended by manufacturer (Promega, Wisconsin, USA). Digested fragments were separated by electrophoresis on 2.5 % agarose gel and visualized with ethidium bromide staining. The allele resulting in the formation of an 170 bp fragment (Hsp92II cutting site absent) was designated as L allele and that generating both 126 bp and 44 bp fragments as M allele. The verification of correct genotypes in gel was based on comparison of previously known genotype standards.

Serum PON activity was measured based on its capacity to hydrolyse paraoxon and by monitoring p-nitrophenol formation. In the assay, 25 $\mu$l serum was added into 800 $\mu$l of 0.0125 M borate buffer (pH 7.5) containing 300 $\mu$M $CaCl_2$. After preincubation for 2 min, the reaction was started by adding the substrate (100 $\mu$l of 3 mM paraoxon) and the reaction mixture was incubated at 37° C. for 30 min. The reaction was stopped by adding 100 $\mu$l of 0.5 M trichloroacetic acid. The absorbance of the sample was monitored at 405 nm and paraoxonase activity was calculated using p-nitrophenol as a standard.

The kit for use in the method according to the invention preferably contains the various components needed for carrying out the method packaged in separate containers and/or vials and including instructions for carrying out the method. Thus, for example, some or all of the various reagents and other ingredients needed for carrying out the determination, such as buffers, primers, enzymes, control samples or standards etc can be packaged separately but provided for use in the same box. Instructions for carrying out the method can be included inside the box, as a separate insert, or as a label on the box and/or on the separate vials.

Testing for the Risk of Cancer

The study subjects were from the "Kuopio Ischaemic Heart Disease Risk Factor Study" (KIHD), a prospective population study to investigate risk factors for cardiovascular diseases, diabetes and cancers.[11–15,17,18] The study protocol was approved by the Research Ethics Committee of the University of Kuopio. The study sample comprised men from Eastern Finland aged 42, 48, 54 or 60 years. A total of 2,682 men were examined during 1984–89. All participants gave a written informed consent. Men with a history of cancer, either self-reported or registered in the national cancer registry before entry to KIHD and those who died of a cardiovascular cause during the follow-up were excluded. Of those remaining, a DNA sample was available for 1,518 men.

All cancer cases in the health care have been reported to a national cancer registry in Finland since 1953.[16] Our study cohort was record-linked to this cancer registry data by using the unique personal identification code (social security number) that all Finns have.[17] The first occurrence of cancer after the KIHD baseline examination was registered in the cancer registry during 1984–97 for 52 cohort members. The primary site was prostate for 13, gastro-intestinal for 13, lung for eight, other genital or urinary for six and another organ system for 12 cancers.

Lipoproteins were separated from fresh serum samples using ultracentrifugation and precipitation.[12,13] The proportion of electronegatively charged LDL of total plasma LDL was determined at the 11-year follow-up for 232 consecutive participants by an FPLC method.[18] Cholesterol and triglyceride concentrations were measured enzymatically, plasma ascorbate and lipid-standardized plasma vitamin E concentration by HPLC methods[14,19] serum ferritin with a RIA[12] and urinary excretion of nicotine metabolites with a colorimetric method.[20] The maximal oxygen uptake, a measure of cardiorespiratory capacity, was measured directly during a symptom limited exercise test.[13]

Information regarding medical history and medications was obtained by interview. Smoking was recorded using a self-administered questionnaire and the dietary intake of nutrients was estimated by four-day food recording.[15]

Differences in risk factors between PON1 genotypes were tested for statistical significance with the Student's t-test allowing for unequal variances. Risk-factor adjusted relative risks of cancer were estimated by multivariate Cox proportional hazards model. Covariates were selected by forward step-up modelling, using P-value of 0.10 as entry criterium. Missing values in covariates were replaced by grand means. All tests of significance were two-sided. The statistical analyses were performed with either SPSS software for IBM RS/6000 workstation or SPSS 8.0 for Windows 97.

Of the cohort members, 170 (11.2%) were MM homozygous, 701 (46.2%) heterozygous and 647 (42.6%) LL homozygous. Allele M carriers were combined to one group, and this group was compared with the LL homozygotes. The distribution of selected baseline risk factor characteristics in the two PON1 genotype groups are shown in Table 1. There were neither statistically nor biologically significant differences in the distribution of any of the measured cancer risk factors between the two groups.

To ascertain the penetrance of the PON1 54 mutation, serum PON activity was measured for a subsample of 87 cohort members as described above. The mean activity was 104.3 nmol/ml/min in LL homozygotes vs. 56.9 nmol/ml/min in M54 carriers (p<0.001). The mean proportion of electronegatively charged LDL of total LDL was 5.4% in 97 LL homyzygotes, 5.9% in 117 heterozygotes and 6.9% in 28 MM homozygotes (p=0.033).

Figure 1:
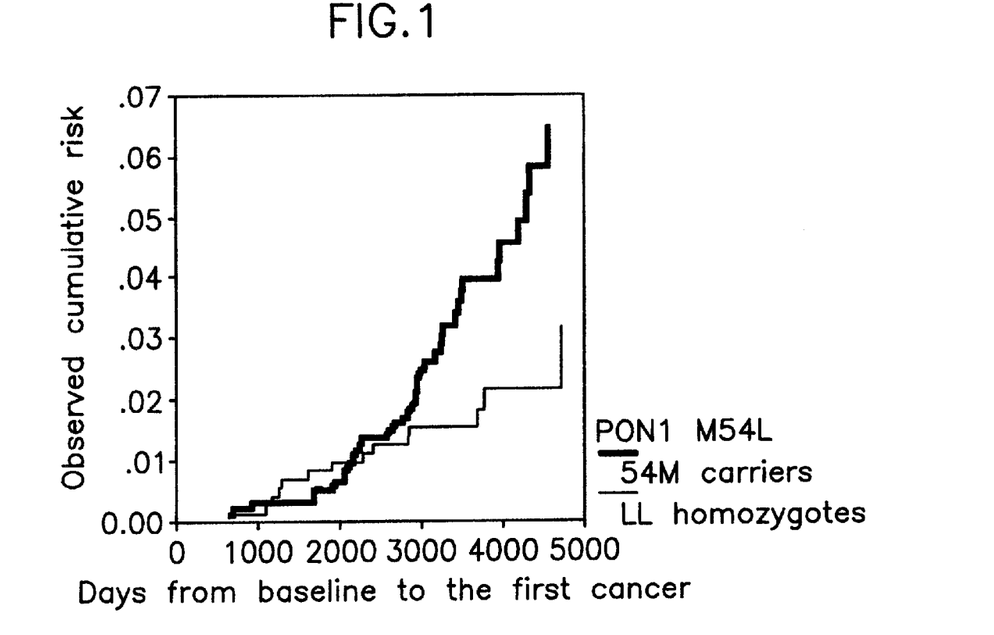
FIG. 1 shows the risk-factor-adjusted cumulative risk of any cancer in the two PON1 genotype groups during the follow-up at the mean of covariates.
Figure 2:
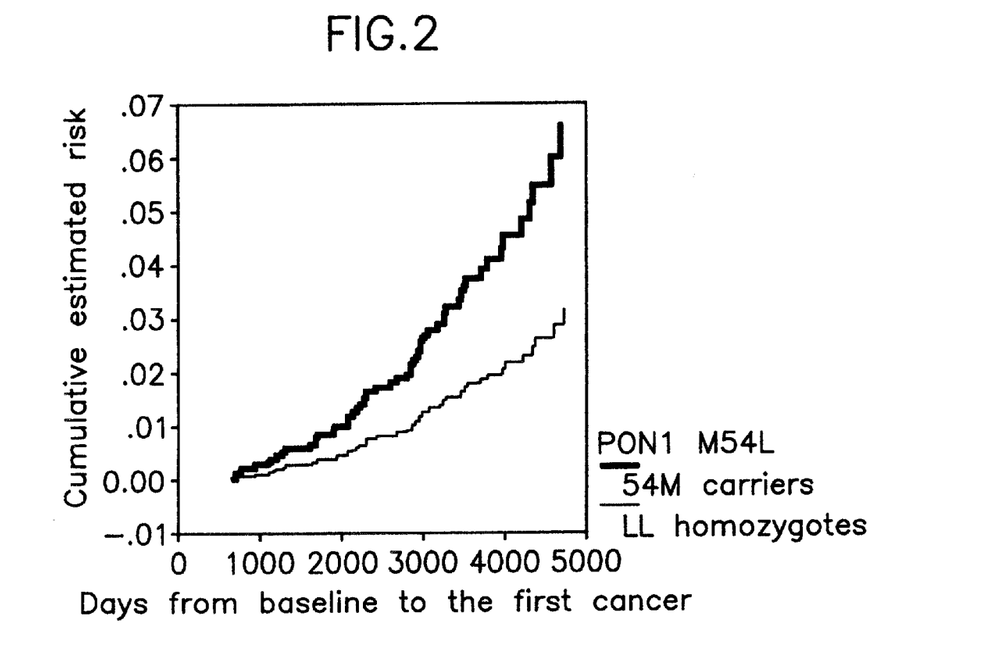
FIG. 2 shows the risk-factor-adjusted estimated cumulative risk of cancer during the follow-up in the allele M carriers and LL homozygotes of the PON1 54 polymorphism; smoking status is set to non-smoking.

In a multivariate Cox model adjusting for the strongest other risk factors in this cohort: age, maximal oxygen uptake, smoking status (current smoker vs. non-smoker), serum ferritin, place of residence (urban vs. rural) and examination date, the relative risk of any cancer in LL homozygotes was 0.48 (95% CI 0.26 to 0.89, p=0.019), compared with M54 carriers (p<0.001 for the model, Table 2). The deletion of any single covariate or any combination of covariates or the addition of any measurement concerning smoking habit, diet, plasma antioxidants, drugs, or other diseases did not affect either the magnitude of this relative risk or its statistical significance. The risk-factor-adjusted cumulative risk of any cancer in the two PON1 genotype groups during the follow-up at the mean of covariates is shown in FIG. 1. FIG. 2. shows the risk-factor-adjusted estimated cumulative risk of cancer during the follow-up (cumulative hazard function at mean of the covariates shown in Table 2) in the allele M carriers and LL homozygotes of the PON1 54 polymorphism; smoking status is set to non-smoking.

The protective impact of PON1 LL homozygosity was greatest on prostate and other genito-urinary cancers (Table 3). The relative risk for all genito-urinary cancers was 0.21 (95% CI 0.06, 0.75, p=0.017) in a model including age, serum ferritin, cholesterol lowering medication and urban place of residence as covariates. The association was weaker for other sites.

The allele L which is considered the mutant allele, was remarkably common in our study population, based on a random population sample.

The L allele has consistently been associated with an increased paraoxonase activity in human serum.[4–6, 21] However, Mackness and coworkers reported recently a greater inhibition of lipid peroxide formation in isolated low-density lipoprotein by HDL isolated from MM homozygous persons than by that from persons with other genotypes.[7] In opposite, we observed higher levels of electronegatively charged LDL, a measure of lipid peroxidation in vivo, in the MM homozygous than other men. This finding is consistent with the hypothesis that there was less lipid peroxidation, possibly reflecting lesser oxidative stress, among men who carried the PON1 54 L allele.

The association between the PON1 54 genotype and the risk of cancer is strong in our data. Also, the risk reducing genotype is common, of our study population, 43% had it. According to our data, as much as 18% of all incident cancers in our healthy cohort of middle-aged men would be attributable to this single genetic polymorphism through either direct causation or linkage to other genes. This is the highest attributable fraction that any genetic trait has been reported to account for the risk of cancer.

Testing for the Risk of Coronary Heart Disease

The study subjects were those from the above mentioned "Kuopio Ischaemic Heart Disease Risk Factor Study" (KIHD). Men with prevalent CHD at base-line (n=677) were excluded. Prevalent CHD was defined as either a history of acute coronary event (ACE) or angina pectoris, positive angina pectoris on effort, or use of nitroglycerin tablets at least weekly. Of the remaining 2,005 men, a DNA sample was available for 1,263 men.

The province of Kuopio participated in the multinational MONICA (MONItoring of Trends and Determinants in CArdiovascular Disease) project,[22] in which detailed diagnostic information of all heart attacks during 1982–92 was collected prospectively and subjected to diagnostic classification. Data on acute coronary events between January 1993 and December 1996 was collected from hospitals and classified. The follow-up time was between 27 days and 12 ¾ years, mean 9.0 years. Of the 117 acute coronary events, 56 were classified as definite acute myocardial infarction (AMI), 37 a suspected AMI and 24 prolonged typical chest pain lasting for 20 minutes or more.

The KIHD examination protocol and measurements have been described.[11,13,15,18,23–26] Subjects came to give fasting venous blood samples and hair specimens in the morning, instructed to abstain from ingesting alcohol for three days, and from smoking and eating for 12 hours. Blood was drawn after 30-minute supine rest. DNA extraction and paraoxonase genotyping took place as described earlier.

Lipoproteins (VLDL, LDL and HDL) were separated from fresh serum samples using ultracentrifugation followed by direct VLDL removal and LDL precipitation and HDL2 and $HDL_3$ subfractions by ultracentrifugation.[23] The proportion of electronegatively charged LDL of total plasma LDL was determined at the 11-year follow-up by a liquid chromatographic method in fresh EDTA-plasma.[18] Cholesterol and triglyceride concentrations were measured enzymatically, apolipoprotein B concentration with an immunoturbidimetric method (KONE, Espoo, Finland), plasma fibrinogen concentrations from fresh plasma samples (Coagulometer KC4, Heinrich Amelung, Germany) based on clotting of diluted plasma with excess thrombin and blood glucose by glucose dehydrogenase method (Merck, Darmstadt, Germany). Diabetes was defined as fasting blood glucose of >6.7 mmol/L or dietary or oral treatment for diabetes. Blood haemoglobin was assayed photometrically by cyanmethemoglobin method, haematocrit by haematocrit centrifuge, plasma vitamin C concentration by a high-performance liquid chromatographic method,[19] and hair mercury content by flow injection analysis with cold vapour atomic spectrometry and amalgamation,[25] 24-hour urinary nicotine metabolite excretion with a calorimetric method,[25] serum selenium by atomic absorption spectrometry and ferritin with a radioimmunoassay.[25]

The blood pressure was measured in the morning using a random-zero muddler sphygmomanometer (Hawksley, London, UK) three times in supine, once standing and twice in sitting position. The mean of all six systolic measurements was used. Cardiorespiratory fitness was estimated by maximal oxygen uptake of the subject. The respiratory gas exchange was measured directly during a symptom limited excercise test. The highest average eight second oxygen uptake during a linear workload increase of 20W/min was defined as the maximal oxygen uptake.[13]

Information regarding medical history and medications was obtained by interview. The number of cigarettes, cigars and pipefuls of tobacco smoked daily and the duration of regular smoking in years were recorded using a self-administered questionnaire, checked by an interviewer. Alcohol consumption and hangover frequency in the previous 12 months were assessed with the Nordic Alcohol Consumption Inventory. Socioeconomic status was assessed by a summary scale.[26] The dietary intake of nutrients was estimated using Nutrica software (KELA, Helsinki, Finland) and four-day food recording.[15] Energy expediture of conditioning leisuretime physical activity was estimated with a 12 month questionnaire.[13]

Differences in risk factors between PON1 genotypes were tested for statistical significance with the Student's t-test allowing for unequal variances as described above. Of the 1263 cohort members, 146 (11.6%) were MM hornozygous, 582 (46.1%) heterozygous and 535 (42.4%) LL homozygous. To ascertain the penetrance of the PON1 54 mutation, serum PON activity was measured for a subsample of 123 cohort members as described above. The mean activity was 34.0 (SD 34.0) nmol/ml/min in 11 MM homozygotes, 64.8 (SD 38.3) in 62 heterozygotes and 102.5 (SD 53.5) nmol/ml/min in 50 LL homozygotes (P<0.001 for trend). The mean proportion of electronegatively charged LDL of total LDL was 6.9% in 28 MM homozygotes, 5.9% in 117 heterozygotes and 5.4% in 97 LL homozygotes (P=0.033). Distributions of coronary risk factors entered or tested for entry as covariates in analyses concerning the association of the PON1 genotype with ACE risk are shown in Table 4 separately for MM homozygotes and allele L carriers. None of the differences between genotypes were either biologically or statistically significant.

There was no statistically significant difference in the risk of ACE between the heterozygotes and the LL homozygotes. The MM homozygous men had a 2.2-fold (95% confidence interval 1.4 to 3.4, P<0.001) risk of ACE in a Cox model adjusting for 11 other strongest risk factors (including blood haemoglobin, diabetes, ischaemia in exercise test, serum apolipoprotein B, cigarette pack-years and serum ferritin) compared with the allele L carriers (Table 5, Model 1). The addition of the variable indicating family history of CHD and serum $HDL_2$ cholesterol concentration in the model did not affect the impact of PON1 MM homozygosity on ACE risk notably (Table 5, Model 2).

Figure 3:
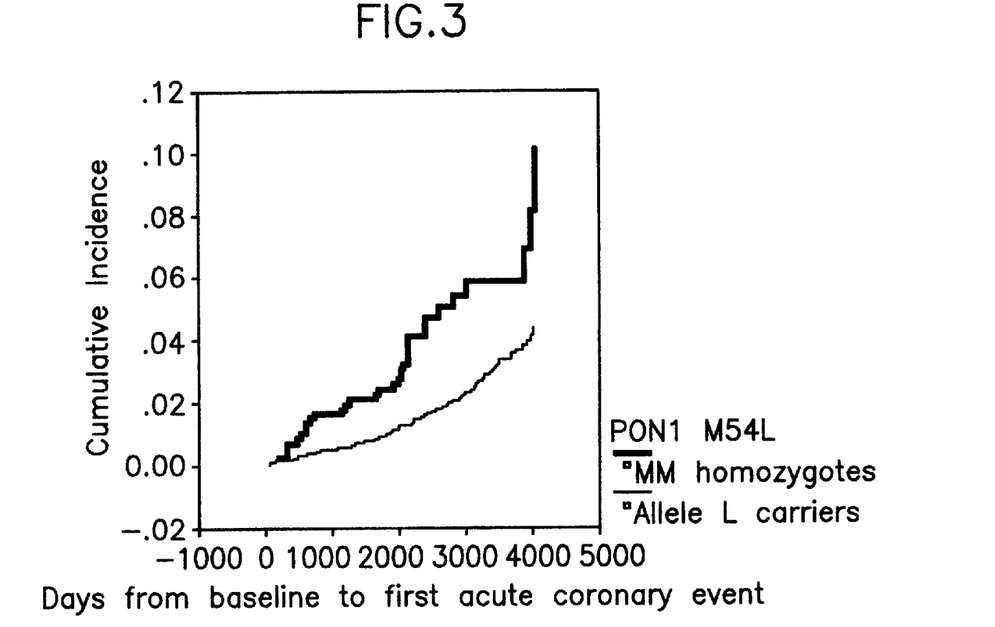
FIG. 3 shows the cumulative incidence of acute coronary event during the follow-up in MM homozygotes and allele L carriers of the PON1 54 polymorphism.
Figure 4:
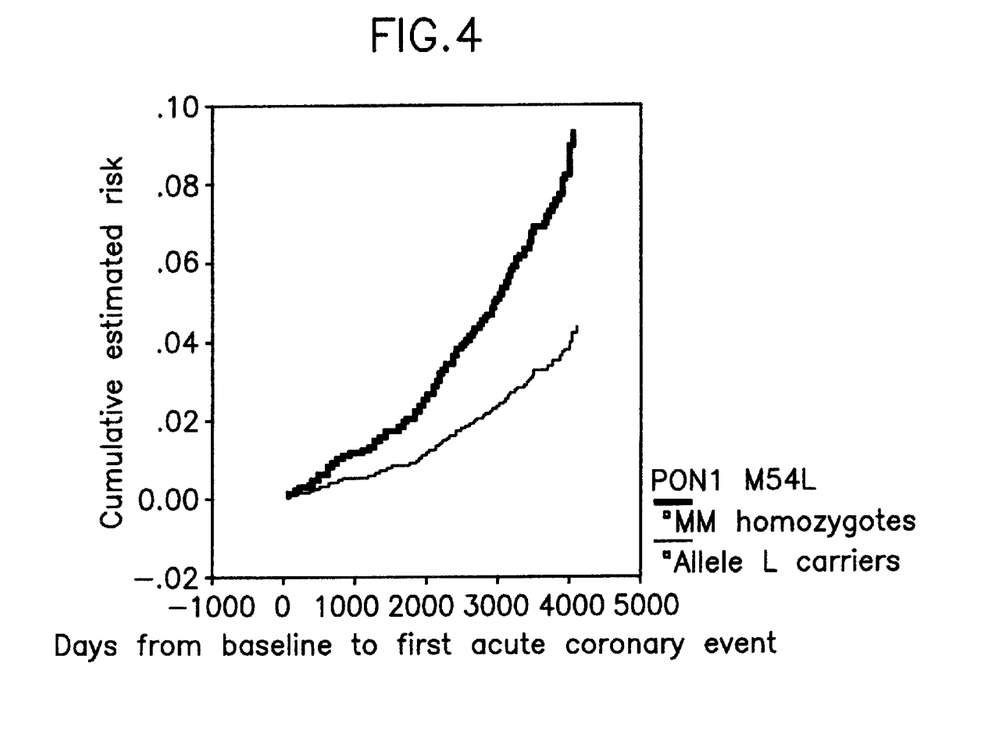
FIG. 4 shows the estimated cumulative risk of acute coronary event during the follow-up in MM homozygotes and allele L carriers of the PON1 54 polymorphism.

The excess risk of ACE among PON1 MM homozygotes was greater in smokers (relative risk 3.4, 95% CI 1.6 to 7.2, P=0.002) than in non-smokers (1.7, 95% CI 1.0 to 3.1, P=0.060) (Table 6). The impact of serum apolipoprotein B, dietary iron intake and vitamin C deficiency was greater and the impact of $HDL_2$ cholesterol on ACE risk smaller in smokers than in non-smokers. FIG. 3. shows the cumulative incidence of acute coronary event during the follow-up in MM homozygotes and allele L carriers of the PON1 54 polymorphism, and FIG. 4. shows the estimated cumulative risk of acute coronary event during the follow-up in MM homozygotes and allele L carriers of the PON1 54 polymorphism, at mean of covariates in model 2, Table 5 (binary risk factors set a zero).

We also analyzed whether the impact of the major traditional risk factors differed in men with different PON1 genotypes (Table 7). The association of the hair mercury content, dietary arsene intake, serum selenium concentration and 24-hour urinary excretion of nicotine metabolites, a quantitative measure of smoking, serum $HDL_2$ cholesterol concentration and family history of CHD with ACE was stronger and that for diabetes and serum total cholesterol concentration was weaker in allele M carriers than in LL homozygotes. The difference between genotypes in the adjusted relative risk for hair mercury content was statistically significant (P<0.05).

In our present prospective population-based cohort study, men who were MM homozygous for the Met54Leu polymorphism of the PON1 gene, had over twofold risk of the first ACE, compared with men with other PON1 54 genotypes. Persons possessing the M allele have been previously shown to have reduced plasma PON activity.[8] We also confirmed this in a subgroup of our study cohort members. The MM homozygous men had 58 percent reduced serum PON activity. This observation supports the hypothesis that persons with low PON levels have an increased risk of ACE. In accordance with this, we observed 21 percent higher levels of electronegatively charged LDL, a measure of lipid peroxidation in vivo, in the MM homozygous men than others. This finding is consistent with the hypothesis that there was less lipid peroxidation, presumably reflecting lesser oxidative stress, among men who carried the PON1 54 L allele.

The impact of serum $HDL_2$ cholesterol concentration on RICE risk was smaller in LL homozygous men than others. This suggests that HDL concentration might be less important if the PON enzyme is effective but becomes more critical in persons whose PON enzyme is less effective, such as the allele M carriers. The deleterious effect of smoking, high hair mercury content and dietary intake of arsene was stronger in allele M carriers. This could plausibly be due to the less effective antioxidative defence in allele M carriers. Smoking[27] and mercury compounds[28] have been found to inhibit serum PON activity. On the basis of this, we expected the effect of smoking and high hair mercury content on ACE risk to be larger in allele M carriers. This was the finding in our study. The observation suggests that in conditions of increased oxidative stress, the protective role of PON is even more important. The PON1 MM homozygosity appears to synergistically enhance the coronary risk increasing effect[25] of mercury accumulation in the body.

According to our present findings, persons with low PON due to MM homozygous PON genotype are at markedly increased risk of ACE. On the other hand, persons with the LL homozygosity of POIVI genotype appear to possess a genetic trait that protects them against ACE.

The association between the PON genotype and the risk of ACE is strong in our data, among the strongest than for any other risk factor that we measured in our study cohort.

TABLE 1

Baseline distributions of risk factors for cancer among men with different PON1 54 genotypes

| | LL homozygotes (n = 647) | | | | M54 carriers (n = 871) | | | |
|---|---|---|---|---|---|---|---|---|
| Characteristic | Mean | SD | Minimum | Maximum | Mean | SD | Minimum | Maximum |
| Age (years) | 52.6 | 5.6 | 42.0 | 61.3 | 52.6 | 5.8 | 42.0 | 61.2 |
| Cigarette-years | 138 | 279 | 0 | 2115 | 140 | 302 | 0 | 2700 |
| Urinary nicotine metabolite excretion (mg/d) | 5.5 | 7.2 | 0.0 | 59.4 | 5.5 | 7.2 | 0.0 | 56.9 |
| Maximal oxygen uptake (ml/kg/min) | 31.1 | 7.2 | 8.3 | 58.2 | 31.4 | 7.2 | 6.4 | 55.5 |
| Serum ferritin ($\mu$g/l) | 172 | 173 | 13 | 2270 | 162 | 130 | 9 | 835 |
| Serum cholesterol (mmol/l) | 5.84 | 1.09 | 2.60 | 14.40 | 5.95 | 1.05 | 3.43 | 10.09 |
| Serum HDL cholesterol (mmol/l) | 1.29 | 0.30 | 0.55 | 2.92 | 1.30 | 0.30 | 0.58 | 2.78 |
| Serum triglycerides (mmol/l) | 1.34 | 0.80 | 0.20 | 7.03 | 1.35 | 0.84 | 0.27 | 10.93 |
| Body-mass index (kg/m2) | 26.7 | 3.2 | 19.0 | 40.3 | 26.7 | 3.4 | 18.8 | 48.6 |
| Waist-to-hip circumference ratio | 0.94 | 0.06 | 0.75 | 1.73 | 0.95 | 0.06 | 0.78 | 1.51 |
| Plasma ascorbate ($\mu$mol/l) | 48.2 | 23.2 | 1.7 | 123.3 | 49.3 | 22.3 | 2.8 | 137.5 |
| Plasma lipid-standardized vitamin E | 1.01 | 0.19 | 0.37 | 1.97 | 1.00 | 0.21 | 0.41 | 2.22 |
| Current smoker | 28.4% | | | | 29.4% | | | |
| Urban residence | 73.6% | | | | 73.3% | | | |

SD denotes standard deviation.

TABLE 2

The strongest risk factors for cancer of any site in a multivariate Cox regression model in 1,518 healthy men

| | Relative risk* | 95% CI | p-value |
|---|---|---|---|
| PON1 54 genotype (LL vs. other) | 0.48 | 0.26, 0.89 | 0.019 |
| Maximal oxygen uptake (per ml/kg/min) | 0.95 | 0.91, 0.99 | 0.014 |
| Age (per year) | 1.08 | 1.01, 1.15 | 0.028 |
| Place of residence (urban vs. rural) | 2.00 | 0.97, 4.12 | 0.060 |
| Serum ferritin (per 100 $\mu$g/l) | 1.13 | 0.99, 1.29 | 0.067 |
| Smoking status (yes vs. no) | 1.65 | 0.93, 2.91 | 0.085 |
| Entire model | | | <0.001 |

*The model included also the date of examination (in months from the first date) as a covariate.

TABLE 3

Number of men who developed cancer of those in the two PON1 54 genotypes and relative risks for site-specific cancers

| Cancer type | Number of men who developed cancer | | Relative risk (95% CI)* | p-value* |
|---|---|---|---|---|
| | LL homozygotes | M carriers | | |
| Gastrointestinal | 4 | 9 | 0.63 (0.19, 2.06) | 0.45 |
| Prostate | 2 | 11 | 0.22 (0.05, 1.04) | 0.06 |
| Other genitourinary | 1 | 5 | 0.21 (0.02, 2.08) | 0.18 |
| Lung | 3 | 5 | 0.61 (0.14, 2.66) | 0.51 |
| Other | 4 | 8 | 0.68 (0.21, 2.26) | 0.53 |
| Any cancer | 14 | 38 | 0.48 (0.26, 0.89) | 0.02 |

*From Step-up Cox models (PIN 0.10 for entry) with a varying number of covariates.

TABLE 4

BASE-LINE DISTRIBUTIONS OF CORONARY RISK FACTORS AMONG MEN IN DIFFERENT PARAOXONASE 54 GENOTYPES

| CHARACTERISTIC | GENOTYPE LL OR LM (N = 1117) | | | | GENOTYPE MM (N = 146) | | | |
|---|---|---|---|---|---|---|---|---|
| | Mean | SD | Minimum | Maximum | Mean | SD | Minimum | Maximum |
| Age (years) | 52.2 | 5.7 | 42.0 | 61.2 | 51.9 | 5.7 | 42.1 | 60.9 |
| Adulthood socioeconomic status () | 7.7 | 4.1 | 0 | 17 | 7.2 | 4.3 | 0 | 15 |
| Serum total cholesterol (mmol/L) | 5.87 | 1.04 | 2.60 | 14.40 | 6.00 | 1.14 | 3.43 | 9.69 |
| Serum HDL cholesterol (mmol/L) | 1.31 | 0.29 | 0.57 | 2.78 | 1.28 | 0.29 | 0.74 | 2.46 |
| Serum $HDL_2$ cholesterol (mmol/L) | 0.86 | 0.27 | 0.07 | 2.26 | 0.86 | 0.27 | 0.33 | 1.75 |
| Serum triglycerides (mmol/L) | 1.30 | 0.77 | 0.20 | 10.9 | 1.35 | 0.89 | 0.42 | 7.84 |
| Serum apolipoprotein B (g/L) | 1.02 | 0.22 | 0.19 | 1.77 | 1.06 | 0.24 | 0.55 | 1.86 |
| Mean resting systolic blood pressure (mmHg) | 133.4 | 15.6 | 99.0 | 201.3 | 134.1 | 17.9 | 99.0 | 194.0 |
| Antihypertensive medication (yes vs. no) | 13.5% | NA | NA | NA | 16.4% | NA | NA | NA |
| Cigarette-years | 138 | 300 | 0 | 2700 | 117 | 255 | 0 | 1350 |
| 24-h urinary nicotine metabolite excretion (mg/d) | 5.4 | 7.4 | 0.0 | 59.4 | 4.9 | 6.2 | 0.0 | 41.2 |
| Body-mass index ($kg/m^2$) | 26.6 | 3.2 | 18.8 | 48.6 | 26.6 | 3.9 | 19.2 | 46.7 |
| Diabetes (yes vs. no) | 4.1% | NA | NA | NA | 3.4% | NA | NA | NA |
| Ischemia in exercise test (yes vs. no) | 18.1% | NA | NA | NA | 16.4% | NA | NA | NA |
| Family history of CHD (yes vs. no) | 46.9% | NA | NA | NA | 52.1% | NA | NA | NA |
| Blood haemoglobin (g/L) | 147.1 | 8.9 | 118 | 181 | 147.9 | 10.3 | 105 | 181 |
| Blood haematocrit (%) | 43.0 | 2.4 | 35 | 51 | 43.3 | 2.6 | 34 | 51 |
| Plasma fibrinogen (g/L) | 2.97 | 0.54 | 1.72 | 6.71 | 2.92 | 0.56 | 1.77 | 4.77 |
| Plasma vitamin C (<11.4 µmol/L) | 4.6% | NA | NA | NA | 4.1% | NA | NA | NA |
| Serum selenium (µg/L) | 119.8 | 15.3 | 0.6 | 217.0 | 119.9 | 14.9 | 75.0 | 161.0 |
| Serum ferritin (≧200 µ/L vs. <200 µg/L) | 26.5% | NA | NA | NA | 26.0% | NA | NA | NA |
| Hair mercury content (ppm) | 1.75 | 1.72 | 0.0 | 13.0 | 1.71 | 1.73 | 0.0 | 11.2 |
| Dietary iron intake (mg/d) | 18.8 | 5.8 | 2.5 | 64.5 | 18.4 | 5.2 | 9.4 | 41.3 |
| Dietary arsene intake (µg/d) | 47.6 | 30.4 | 8.7 | 354.6 | 45.8 | 27.1 | 14.9 | 203.6 |

TABLE 5

THE STRONGEST RISK FACTORS FOR ACUTE CORONARY EVENT IN MULTIVARIATE MODELS

| RISK FACTOR | MODEL 1 | | | MODEL 2 | | |
|---|---|---|---|---|---|---|
| | RELATIVE RISK | 95 PERCENT CONFIDENCE INTERVAL | P-VALUE | RELATIVE RISK | 95 PERCENT CONFIDENCE INTERVAL | P-VALUE |
| Paraoxonase genotype MM (yes vs. other) | 2.17 | 1.37, 3.44 | <0.001 | 2.14 | 1.35, 3.39 | 0.001 |
| Blood haemoglobin (g/L) | 1.03 | 1.01, 1.05 | 0.001 | 1.03 | 1.01, 1.05 | 0.004 |
| Diabetes (yes vs. no) | 2.58 | 1.45, 4.61 | 0.001 | 2.29 | 1.28, 4.11 | 0.006 |
| Ischemia in exercise test (yes vs. no) | 1.91 | 1.28, 2.86 | 0.002 | 1.82 | 1.22, 2.73 | 0.004 |
| Hair mercury (≧2.0 ppm vs. <2.0 ppm) | 1.69 | 1.15, 2.46 | 0.007 | 1.78 | 1.21, 2.60 | 0.003 |
| Serum apolipoprotein B (g/L) | 2.94 | 1.31, 6.59 | 0.009 | 1.96 | 0.83, 4.64 | 0.126 |
| Adulthood socioeconomic status | 1.06 | 1.01, 1.11 | 0.015 | 1.07 | 1.02, 1.12 | 0.007 |
| Plasma vitamin C (<11.4 vs. ≧11.4 µmol/L) | 2.04 | 1.10, 3.79 | 0.024 | 2.13 | 1.15, 3.98 | 0.017 |
| Cigarette pack-years | 1.01 | 1.0004, 1.02 | 0.042 | 1.01 | 1.0001, 1.02 | 0.048 |

TABLE 5-continued

THE STRONGEST RISK FACTORS FOR ACUTE CORONARY EVENT IN MULTIVARIATE MODELS

| RISK FACTOR | MODEL 1 | | | MODEL 2 | | |
|---|---|---|---|---|---|---|
| | RELATIVE RISK | 95 PERCENT CONFIDENCE INTERVAL | P-VALUE | RELATIVE RISK | 95 PERCENT CONFIDENCE INTERVAL | P-VALUE |
| Serum ferritin ($\geq$200 $\mu$g/L vs. <200 $\mu$g/L) | 1.45 | 0.97, 2.16 | 0.073 | 1.45 | 0.97, 2.18 | 0.073 |
| Dietary iron intake (mg/d) | 1.02 | 0.99, 1.05 | 0.172 | 1.02 | 0.99, 1.05 | 0.184 |
| Serum selenium ($\mu$g/L) | 0.99 | 0.98, 1.008 | 0.482 | 0.99 | 0.98, 1.01 | 0.525 |
| Family history of coronary heart disease (yes vs. no) | | | | 1.72 | 1.18, 2.52 | 0.005 |
| Serum HDL$_2$ cholesterol (mmol/L) | | | | 0.37 | 0.16, 0.82 | 0.015 |
| Entire model | | | <0.001 | | | <0.001 |

TABLE 6

THE STRONGEST RISK FACTORS FOR ACUTE CORONARY EVENT IN MULTIVARIATE MODELS IN NON-SMOKERS AND SMOKERS.

| RISK FACTOR | NON-SMOKERS (N = 912) | | | SMOKERS (N = 351) | | |
|---|---|---|---|---|---|---|
| | RELATIVE RISK | 95 PERCENT CONFIDENCE INTERVAL | P-VALUE | RELATIVE RISK | 95 PERCENT CONFIDENCE INTERVAL | P-VALUE |
| Paraoxonase genotype MM (yes vs. other) | 1.73 | 0.98, 3.07 | 0.06 | 3.37 | 1.57, 7.24 | 0.002 |
| Serum apolipoprotein B (g/L) | 1.61 | 0.59, 4.38 | 0.349 | 4.42 | 0.97, 20.19 | 0.055 |
| Dietary iron intake (mg/d) | 1.00 | 0.96, 1.04 | 0.867 | 1.06 | 1.01, 1.12 | 0.018 |
| Plasma vitamin C (<11.4 vs. $\geq$11.4 $\mu$mol/L) | 0.99 | 0.31, 3.16 | 0.923 | 2.41 | 1.14, 5.11 | 0.022 |
| Systolic blood pressure (mmHg) | 1.01 | 1.00, 1.03 | 0.073 | 1.02 | 1.002, 1.04 | 0.026 |
| Serum HDL$_2$ cholesterol (mmol/L) | 0.20 | 0.07, 0.59 | 0.004 | 0.58 | 0.16, 2.12 | 0.408 |
| Number of men who developed ACE | 74 | | | 43 | | |
| Entire model | | | <0.001 | | | <0.001 |

Both models included additionally age (years) and three indicator variables for examination years.

TABLE 7

THE STRONGEST RISK FACTORS FOR ACUTE CORONARY EVENT IN MEN IN DIFFERENT PARAOXONASE M54L GENOTYPES IN MULTIVARIATE MODELS

| RISK FACTOR | GENOTYPE LL (N = 535) | | | GENOTYPE MM OR ML (N = 728) | | |
|---|---|---|---|---|---|---|
| | RELATIVE RISK | 95 PERCENT CONFIDENCE INTERVAL | P-VALUE | RELATIVE RISK | 95 PERCENT CONFIDENCE INTERVAL | P-VALUE |
| Serum total cholesterol (mmol/L) | 1.62 | 1.30, 2.04 | <0.001 | 1.08 | 0.85, 1.384 | 0.538 |
| Serum HDL2 cholesterol (mmol/L) | 0.66 | 0.19, 2.31 | 0.516 | 0.19 | 0.07, 0.51 | <0.001 |
| Hypertension (yes vs. no) | 1.75 | 0.96, 3.19 | 0.067 | 1.78 | 1.06, 2.99 | 0.029 |
| Diabetes (yes vs. no) | 7.30 | 3.25, 16.40 | <0.001 | 1.11 | 0.44, 2.77 | 0.829 |
| 24-h urinary excretion of nicotine metabolites (mg/d) | 1.02 | 0.98, 1.06 | 0.313 | 1.03 | 1.01, 1.05 | 0.009 |
| Hair mercury (ppm) | 1.01 | 0.88, 1.16 | 0.844 | 1.21 | 1.06, 1.38 | 0.004 |
| Dietary arsene intake ($\mu$g/d) | 1.00 | 0.98, 1.01 | 0.592 | 1.01 | 1.0003, 1.01 | 0.040 |
| Serum selenium ($\mu$g/L) | 1.00 | 0.98, 1.02 | 0.884 | 0.98 | 0.96, 0.996 | 0.013 |
| Family history of CHD (yes vs. no) | 1.32 | 0.75, 2.32 | 0.341 | 2.49 | 1.43, 4.33 | 0.001 |
| Number of men who developed AMI | 51 | | | 66 | | |
| Entire model | | | <0.001 | | | <0.001 |

Both models included additionally age (in years) and three indicator variables for examination years 1987, 1988 and 1989.

REFERENCES

1. Navab M, Berliner J A, Watson Ad et al. The Yin and Yang of oxidation in the development of the fatty streak. A review based on the 1994 George Lyman Duff Memorial Lecture. *Arterioscler Thromb Vasc Biol* 1996; 16:831–42.

2. Mackness M I, Arrol S, Abbott C A, Durrington P N. Protection of low-density lipoprotein against oxidative modification by high-density lipoprotein associated paraoxonase. *Atherosclerosis* 1993; 104:129–35.

3. Watson A D, Berliner J A, Hama S Y, La Du B N, Faul K F, Fogelman A M, Navab M. Protective effect of high density lipoprotein associated paraoxonase. Inhibition of the biological activity of minimally oxidized low density lipoprotein. *J Clin Invest* 1995;96:2882–91.

4a. La Du B N, Adkins S, Kuo C L, Lipsig D. Studies on human serum paraoxonase/arylesterase. *Chem Biol Interact* 1993 June; 87 (1–3):25–34

4. Humbert R, Adler D A, Disteche C M, Hassett C, Omiecinski C J, Furlong C E. The molecular basis of the human serum paraoxonase activity polymorphism. *Nature Genet* 1993; 3: 73–6.

5. Mackness M I, Mackness B, Durrington P N, Connelly P W, Hegele R A. Paraoxonase: biochemistry, genetics and relationship to plasma lipoproteins. *Curr Opin Lipidol* 1996; 7: 69–76.

6. Mackness M I, Arrol S, Mackness B, Durrington P N. Alloenzymes of paraoxonase and effectiveness of high-density lipoproteins in protecting low-density lipoprotein against lipid peroxidation. *Lancet* 1997; 349: 851–2.

7. Mackness B, Durrington P N, Mackness M I. Polymorphisms of paraoxonase genes and low-density lipoprotein peroxidation. *Lancet* 1999; 353: 468–9.

8. Garin M C, James R W, Dussoix P, et al. Paraoxonase polymorphism Met-Leu54 is associated with modified serum concentrations of the enzyme. A possible link between the paraoxonase gene and increased risk of cardiovascular disease in diabetes. *J Clin Invest* 1997; 99: 62–6.

9. Mackness B, Mackness M I, Arrol S, Turkie W, Durrington P N. Effect of the molecular polymorphisms of human paraoxonase (PON1) on the rate of hydrolysis of paraoxon. *Br J Pharmacol* 1997; 122: 265–8.

10. Zama T, Murata M, Matsubara Y, et al. A $^{192}$Arg variant of the human paraoxinase (HUMPONA) gene polymorphism is associated with an increased risk for coronary artery disease in the Japanese. *Arterioscler Thromb Vasc Biol* 1997; 17:3565–9.

11. Salonen J T. Is there a continuing need for longitudinal epidemiologic research? —The Kuopio Ischaemic Heart Disease Risk Factor Study. *Ann Clin Res* 1988; 20: 46–50.

12. Salonen J T, Nyyssönen K, Korpela H, Tuomilehto J, Seppanen R, Salonen R. High stored iron levels are associated with excess risk of myocardial infarction in Eastern Finnish men. *Circulation* 1992; 86: 803–11.

13. Lakka T A, Venäläinen J M, Rauramaa R, Salonen R, Tuomilehto J, Salonen J T. Relation of leisure-time physical activity and cardiorespiratory fitness to the risk of acute myocardial infarction. *N Engl J Med* 1994; 330: 1549–54.

14. Salonen J T, Nyyssönen K, Tuomainen T-P, Maenpaa P H, Korpela H, Kaplan G A, Lynch J, Helmrich S P, Salonen R. Increased risk of non-insulin dependent diabetes mellitus at low plasma vitamin E concentrations: a four year follow-up study in men. *Brit Med J* 1995; 311: 1124–7.

15. Ihanainen M, Salonen R, Seppänen R, Salonen J T. Nutrition data collection in the Kuopio Ischaemic Heart Disease Risk Factor Study: Nutrient intake of middle-aged eastern Finnish men. *Nutr Res* 1989; 9: 89–95.

16. Teppo L, Pukkala E, Lehtonen M. Data quality and quality control of a population-based cancer registry. Experience in Finland. *Acta Oncologica* 1994; 33: 365–9.

17. Everson S A, Goldberg D E, Kaplan G A, et al. Hopelessness and risk of mortality and incidence of myocardial infarction and cancer. *Psychosom Med* 1996; 58: 113–21.

18. Nyyssöonen K, Kaikkonen J, Salonen J T. Characterization and determinants of an electronegatively charged low-density lipoprotein in human plasma. *Scand J Clin Lab Invest* 1996; 56: 681–9.

19. Nyyssönen K, Parviainen M T, Salonen R, Tuomilehto J, Salonen J T. Vitamin C deficiency and risk of myocardial infarction: prospective population study of men from eastern Finland. *Brit Med J* 1997; 314: 634–8.

20. Puhakainen E V J, Barlow R D, Salonen J T. An automated calorimetric assay for urine nicotine metabolites: A suitable alternative to cotinine assays for the assessment of smoking status. *Clin Chim Acta* 1987; 170: 255–62.

21. Mackness M I, Arrol S, Durrington PN. Paraoxonase prevents accumulation of lipoperoxides in low-density lipoprotein. *FEBS Lett* 1991; 286: 152–4.

22. Tuomilehto J, Arstila M, Kaarsalo E, et al. Acute myocardial infarction (AMI) in Finland—baseline data from the FINMONICA AMI register in 1983–1985. *Eur Heart J*. 1992; 13: 577–87.

23. Salonen J T, Salonen R, Seppänen K, Rauramaa R, Tuomilehto J. High density lipoprotein, $HDL_2$ and $HDL_3$ subfractions and the risk of acute myocardial infarction: a prospective population study in Eastern Finnish men. *Circulation* 1991;84: 129–139.

24. Salonen J T, Malin R, Tuomainen T-P, Nyyssönen K, Lakka T A, Lehtimäki T. Polymorphism in the high density lipoprotein paraoxonase gene and the risk of acute myocardial infarction in men: a prospective population-based case-control study. *Brit Med J*, in press.

25. Salonen J T, Seppänen K, Nyyssönen K, et al. Intake of mercury from fish, lipid peroxidation, and the risk of myocardial infarction and coronary, cardiovascular, and any death in eastern Finnish men. *Circulation* 1995; 91:645–55.

26. Kaplan G A, Salonen J T. Socioeconomic conditions in childhood and ischaemic heart disease during middle-age. *Brit Med J* 1990;301:1121–3.

27. Nishio E, Watanabe Y. Cigarette smoke extract inhibits plasma paraoxonase activity by modification of the enzyme's free thiols. *Biochem Biophys Res Commun* 1997;236:289–93.

28. Gonzalvo M C, Gil F, Hernandez A F, Villanueva E, Pla A. Inhibition of paraoxonase activity in human by exposure to EDTA, metals and mercurials. *Chem Biol Interact* 1997; 105: 169–79.

What is claimed is:

1. A method for detecting a risk of prostate, gastrointestinal, urinary, lung or genital cancer in a subject, comprising isolating DNA from said subject, determining the allelic pattern for codon 54 of the paraoxonase encoding PON1 gene in the genomic DNA, whereby identification of M54L mutation indicating said risk being reduced.

2. The method according to claim 1, wherein the allelic pattern is determined using polymerase chain reaction technique.

3. The method according to claim 1, wherein the genomic DNA is isolated from a blood sample from the subject.

4. The method according to claim 1, comprising the additional step of comparing the allelic pattern to known genotype standards.

5. A kit for detecting a risk of prostate cancer, gastrointestinal cancer, urinary cancer, lung cancer, or genital cancer in a subject, comprising means for determining the allelic pattern for the codon 54 of the paraoxonase encoding PON1 gene in a genomic DNA sample, and means for carrying out a comparison of the allelic pattern so determined to known genotype standards.

6. The method according to claim 1, further comprising the additional step of comparing the allelic pattern to a control sample comprising the M54L mutation, wherein said control sample is a positive control.

* * * * *

SEQUENCE LISTING

<160> NUMBER OF SEQ ID NOS: 2

<210> SEQ ID NO 1
<211> LENGTH: 22

```
<212> TYPE: DNA
<213> ORGANISM: Homo sapiens

<400> SEQUENCE: 1
gaagagtgat gtatagcccc ag                                           22

<210> SEQ ID NO 2
<211> LENGTH: 24
<212> TYPE: DNA
<213> ORGANISM: Homo sapiens

<400> SEQUENCE: 2
tttaatccag agctaatgaa agcc                                         24
```